United States Patent [19]

von Fraunberg

[11] 3,997,577

[45] Dec. 14, 1976

[54] MANUFACTURE OF LAVANDULOL AND ITS ESTERS

[75] Inventor: Karl von Fraunberg, Bobenheim, Germany

[73] Assignee: BASF Aktiengesellschaft, Ludwigshafen (Rhine), Germany

[22] Filed: June 20, 1975

[21] Appl. No.: 588,857

[30] Foreign Application Priority Data

July 5, 1974 Germany .......................... 2432235

[52] U.S. Cl. ................. 260/410.9 N; 260/410.9 R; 260/631.5; 260/489; 260/488 H; 260/476 R; 260/486 R

[51] Int. Cl.$^2$ .................... C11C 3/02; C07C 35/00; C07C 69/02

[58] Field of Search ............... 260/410.9 R, 631.5, 260/489, 488 H, 476 R, 486 R, 410.9 N

[56] References Cited

UNITED STATES PATENTS

| | | | |
|---|---|---|---|
| 2,867,668 | 1/1959 | Theimer | 260/489 X |
| 3,700,717 | 10/1972 | Kappeler | 260/631.5 X |
| 3,856,867 | 12/1974 | Ramsden | 260/631.5 X |

OTHER PUBLICATIONS

Helv. Chim. Acta 35, (1952), 2008.
Helv. Chim. Acta 35, (1952), 1656.
Helv. Chim. Acta 34, (1951), 2009.

Primary Examiner—Winston A. Douglas
Assistant Examiner—John F. Niebling
Attorney, Agent, or Firm—Johnston, Keil, Thompson & Shurtleff

[57] ABSTRACT

A process for the manufacture of lavandulol and its esters, starting from the new compound 3,5,5-trimethyl-1,6-heptadien-3-ol, which is converted by conventional methods to 3,5,5-trimethyl-hepta-2,6-dien-1-ol or its esters, which are rearranged to lavandulol or lavandulyl esters by heating at from 150° to 250° C. Using the new process, the desirable product lavandulol, and its esters, which are also of great interest as scents, and even previously unknown lavandulyl esters, can be manufactured simply, in goods yields and in excellent purity, from easily obtainable starting compounds. Both the new starting compound 3,5,5-trimethyl-hepta-1,6-dien-3-ol and the new 3,5,5-trimethyl-hepta-2,6-dien-1-yl esters, obtained as intermediates, are scents and can be employed in the perfumery industry.

12 Claims, No Drawings

MANUFACTURE OF LAVANDULOL AND ITS ESTERS

The invention relates to a process for the manufacture of lavandulol and its esters from the new compound 3,5,5-trimethyl-1,6-heptadien-3-ol, via 3,5,5-trimethyl-2,6-heptadien-1-ol and its esters.

Lavandulol and several of its esters are naturally occurring terpene scents, greatly desired in the perfumery industry. Numerous syntheses for their manufacture have been developed (cf. Helv. Chim. Acta 35 (1952) 2008 and Helv. Chim. Acta 35 (1952) 1656), but all are very involved and expensive.

The simplest known process is the process of Brack et al (cl. Helv. Chim. Acta 34 (cf. (1951) 2009), wherein 3,3-dimethyl-1-hexen-5-one is converted, by condensation with the Grignard compound of ethoxyacetylene, to 3,5,5-trimethyl-3-hydroxy-1-ethoxyhept-6-en-1-yne, the latter is rearranged to ethyl 3,5,5-trimethyl-hepta-2,6-dien-1-oate, by means of dilute sulfuric acid, and this intermediate is again rearranged, by heating to 300° C in bomb tube, to 2,6-dimethyl-5-ethoxycarbonyl-2,6-heptadiene, which can be converted to lavandulol by reduction with LiAlH$_4$. However, lavandulol obtained by this process is heavily contaminated and must be purified by means of phthalic anhydride; this purification is expensive and entails considerable losses. The process described gives lavandulol in a yield of only 27%, based on ethyl 3,5,5-trimethyl-hepta-2,6-dien-1-oate. Direct heating of 3,5,5-trimethyl-hepta-2,6-dienol at 300° C, which has also been described, on the other hand, gives lavandulol in yields of only 1.25% of theory. Both processes are uneconomical, not only because of the low yields and the expense of purification, but because of the expensive and involved reaction steps such as the reaction with ethoxy-acetylene/ethyl-magnesium bromide or the reaction with lithium aluminum hydride.

It is an object of the present invention to provide a process which permits simple and economical manufacture of lavandulol and its esters.

We have found, surprisingly, that lavandulol and lavandulyl esters which are of interest as scents may be manufactured simply and economically by using the new compound 3,5,5-trimethylhepta-1,6-dien-3-ol as the starting material, converting it by conventional methods to 3,5,5-trimethyl-hepta-2,6-dien-1-ol or its esters and heating the resulting 3,5,5-trimethyl-hepta-2,6-dien-1-ol or its esters at from 150° to 250° C.

Accordingly, the invention relates to a process for the manufacture of compounds of the formula I

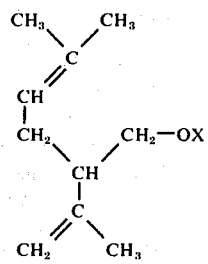
(I)

in which X is H or -CO-R, wherein R is H or an optionally olefinically unsaturated aliphatic hydrocarbon radical of up to 8 carbon atoms, an optionally olefinically unsaturated cycloaliphatic hydrocarbon radical of up to 8 carbon atoms or an aromatic hydrocarbon radical of up to 8 carbon atoms, which may be substituted by substituents which are inert under the reaction conditions, in which process A) the new compound 3,5,5-trimethyl-hepta-1,6-dien-3-ol is converted directly or via a 3,5,5-trimethyl-hepta-2,6-dien-1-yl halide to a 3,5,5-trimethyl-hepta-2,6-diene derivative of the formula II

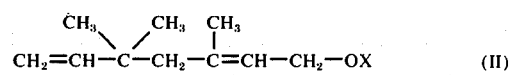
(II)

in which X has the above meaning, and B) the resulting compound of the formula II is heated, if appropriate in a solvent which is inert under the reaction conditions, at from 150° to 250° C, preferably from 170° to 200° C.

The reaction according to the invention can be illustrated by the following equations:

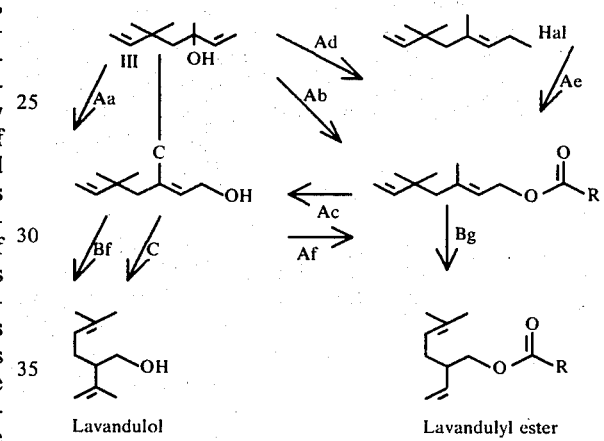

Lavandulol          Lavandulyl ester

To manufacture lavandulol, ie. a compound of the formula I, in which X is H, by the process of the invention, the method used is that in reaction step A, 3,5,5-trimethyl-hepta-1,6-dien-3-ol (III) is converted, by treatment with an acid catalyst at from −50° to +200° C, or by heating in the presence of a catalyst based on a transition metal of sub-groups 5 to 7 at from 50° to 250° C, preferably from 100° to 200° C, in the liquid phase, into 3,5,5-trimethyl-hepta-2,6-dien-1-ol (the compound of the formula II, in which X is H) (Aa); or that in reaction step A 3,5,5-trimethyl-hepta-1,6-dien-3-ol is converted to 3,5,5-trimethyl-hepta-2,6-dien-1-ol (the compound of the formula II, in which X is H) by first reacting compound (III) in the presence of an acid catalyst, with a carboxylic acid of the formula R-CO-OH, in which R has the above meanings, or with the corresponding carboxylic acid anhydride or caboxylic acid halide where available and then hydrolyzing, by conventional methods, the resulting 3,5,5-trimethyl-hepta-2,6-diene derivative of the formula II, in which X is -CO-R (Ab + Ac); or that in reaction step A 3,5,5-trimethyl-hepta-1,6-dien-3-ol is converted to 3,5,5-trimethyl-hepta-2,6-dien-1-ol (the compound of the formula II, in which X is H) by reacting compound III by conventional methods with a halogenating agent such as HL, PL$_3$, PL$_5$, SOL$_2$ and COL$_2$, in which L is halogen, preferably Cl or Br, if appropriate in the presence of dialkylamides, N-alkyl-lactams or tertiary amines, provided these do not prevent the rearrangement to the primary halide, to give a 3,5,5-trimethyl-hepta-2,6-dienyl halide and that this is reacted, by conventional methods, with an alkali metal sat, alkaline earth metal salt or ammonium salt of the carboxylic acid R-COOH, in which R has the above meanings, in a non-aqueous medium in the presence of catalysts, to give the 3,5,5-trimethyl-hepta-2,6-diene derivative of the formula II, in which X is —CO-R, and his derivative is hydrolyzed by conventional methods (Ad + Ae + Ac).

To manufacture lavandulyl sters, ie. compounds of the formula I, in which X is -CO-R, where R has the above meanings, the method used is that in reaction step A 3,5,5-trimethylhepta-1,6-dien-3-ol is converted, by reaction with a carboxylic acid of the formula R-CO-OH, in which R has the above meanings, or with the corresponding carboxylic acid anhydride or the corresponding carboxylic acid halide, in the presence of an acid catalyst, directly into a 3,5,5-trimethyl-hepta-2,6-diene derivative of the formula II, in which X is -CO-R (Ab); or that in reaction step A 3,5,5-trimethyl-heptal-1,6-dien-3-ol is converted to a 3,5,5-trimethyl-hepta-2,6-diene derivative of the formula II, in which X is -CO-R, by first converting it by conventional methods to 3,5,5-trimethyl-hepta-1,6-dien-1-yl chloride or bromide and reacting this by conventional methods with an alkali metal salt, alkaline earth metal salt or ammonium salt of the appropriate carboxylic acid R-CO-OH in a non-aqueous medium in the presence of a catalyst (Ad + Ae); or that 3,5,5-trimethyl-hepta-1,6-dien-3-ol is converted, by treatment with an acid catalyst at from −50° to +200° C, or by heating in the presence of a catalyst based on a transition metal of sub-groups 5 to 7 of the Periodic Table of the Elements, at from 50° to 250° C, in the liquid phase, to 3,5,5-trimethyl-hepta-2,6-dien-1-ol (the compound of the formula II, in which X is H) and this is esterified by conventional methods (Aa + Af).

Which of the three variants is preferred depends essentially on the individual yields of the reaction steps for the particular radical R which is desired.

Of course, lavandulol can also be manufactured by conventional hydrolysis from the lavandulyl esters manufactured according to the invenion. Furthermore, we have found that lavandulol can also be manufactured directly from the new 3,5,5-trimethylhepta-1,6-dien-3-ol by heating the latter, in bulk or dissolved in an inert solvent, preferably a non-polar high-boiling solvent such as paraffin oil, silicone oil, groundnut oil, polyethylene glycol and diphenyl ether, at from 150° to 250° C, preferably at from 180° to 220° C.

The new starting compound used according to the invention, namely 3,5,5-trimethyl-hepta-1,6-dien-3-ol, can be obtained simply by the copper-catalyzed reaction of mesityl oxide with a vinyl-magnesium halide followed by conventional Grignard vinylation, or by conventional ethynylation with subsequent partial hydrogenation of the 3,3-dimethyl-1-hexen-5-one first produced.

The new starting compound has an intense fresh odor resembling menthol so that it can in itself be employed as a scent.

The reaction steps for converting 3,5,5-trimethyl-hepta-1,5-dien-3-ol (III) to a 3,3,5-trimethyl-hepta-2,6-diene derivative of the formula II, designated Aa to Af in the above reaction scheme, will be explained in more detail below:

Aa: to convert III to 3,5,5-trimethyl-hepta-2,6-dien-1-ol (IV), the method followed is, eg., that III is treated, at from −50° to +200° C, with a customary acid for bringing about allyl rearrangements (see R.H. De Wolfe and W. G. Young in Patai "The Chemistry of Alkenes", Interscience Publishers 1964, 711 et seq., which is incorporated herein by reference), or that III is heated, eg. in the presence of a catalyst based on a transition metal of sub-groups 5 to 7 of the Periodic Table of the Elements (also referred to as columns 5b to 7b of the Mendeleef Periodic Table, Handbook of Chem. and Phys., 45th edition, page B-2) at from 50° to 250° C, preferably at from 100° to 200° C, in the liquid phase, in accordance with German Laid-Open Specification 1,965,377.

Examples of acid catalysts which may be used are protic acids of $pK_A$ value less than 6 or about 6, eg. aliphatic or aromatic carboxylic acids such as acetic acid, chloroacetic acid, trichloroacetic acid, trifluoroacetic acid and benzoic acid; aliphatic or aromatic sulfonic acids such as methanesulfonic acid or p-toluenesulfonic acid; inorganic acids such as hydrogen halides (HCl or HBr), sulfuric acid, phosphoric acid, polyphosphoric acid, perchloric acid, acid ion exchangers, zeolites or fuller's earths, and also Lewis acids such as $BF_3$, $AlCl_3$, $ZnCl_2$ and the like.

The acid is in general used in amounts of from 0.001 to 0.5 mole per mole of III, in bulk or in aqueous solution. The reaction temperature may be from −50° to +200° C and the reaction time from 0.1 to 20 hours. Both parameters depend very greatly on the strength ($pK_A$ value) and amount of the acid used as the catalyst.

Possible catalysts based on a transition metal of sub-groups 5 to 7 of the Periodic Table are essentially inorganic or organic derivatives of vanadium, niobium, molybdenum, tungsten and rhenium, as are described in detail in German Published Application 1,965,377 (which is incorporated herein by reference). In particular, ammonium metavanadate, tert.-butyl orthovanadate, tert.-amyl orthovanadate, ammonium molybdate, cyclohexyl orthovanadate and vanadyl acetylacetonate may be used.

In general, from 0.001 to 0.05 mole of catalyst is used per mole of alcohol.

Both variants may be carried out in the presence or absence of a solvent. Solvents which may be used are, in general terms, compounds which are chemically inert towards the catalyst and the reactants. In particular, the chlorinated or non-chlonated aliphatic, alicyclic or aromatic hydrocarbons which are liquid under the reaction conditions, and the ethers conventionally used as solvents, may be employed.

The resulting compound IV has a pleasant smell of dried herbs and fresh hay and may be used as a scent.

Ab: the reaction of III to give a 3,5,5-trimethyl-hepta-2,6-dienyl ester follows the principles described by R. H. Wolfe and W. G. Young, Chem. Reviews 56, (1956) 818 et seq. (which is incorporated herein by reference). Acid catalysts which may be used are the acids described under Aa. If an acid is produced in the course of the reaction, as is the case if carboxylic acid anhydrides and acid chlorides are used, the acid present in the reaction mixture frequently suffices as a catalyst; in other cases, it is advantageous to add small amounts of the corresponding acid R-COOH.

The reaction time and reaction temperature in general depend on the amount and strength of the acid catalyst. For example, if a mixture of BF₃ and acetic anhydride is used in amounts of from 0.1 to 10 mole% at a reaction temperature from −20° to +30° C, reaction times of from 0.5 to 5 hours are employed. Reaction conditions which allow the reactions to be carried out below +30° C are preferred. Solvents, eg., aliphatic or aromatic hydrocarbons, chlorinated hydrocarbons or ethers, may be employed. The process may be carried out batchwise or continuously.

Examples of carboxylic acids R-COOH which may be used are formic acid, acetic acid, propionic acid, butyric acid, isobutyric acid, valeric acid, isovaleric acid, α-methylbutyric acid (as the racemic acid or the d- or 1-form), caproic acid, caprylic acid, acrylic acid, methacrylic acid, crotonic acid, dimethacrylic acid, cyclopentanecarboxylic acid, cyclohexanecarboxylic acid, 4-methyl-cyclohex-3-ene-1-carboxylic acid, benzoic acid, salicylic acid, p-methoxybenzoic acid, cinnamic acid, lactic acid, methoxylactic acid, pyruvic acid, levulic acid and methoxyacetic acid, ie. carboxylic acids of the formula R-COOH, in which R is H or an optionally olefinically unsaturated aliphatic or cycloaliphatic or aromatic hydrocarbon radical of up to 8 carbon atoms, which may have hydroxyl groups, alkoxy groups (e.g., methoxy) or keto groups (e.g., acetyl) as substituents which are inert under the reaction conditions. R is preferably H, $CH_3$-, $CH_3$-$CH_2$, $CH_3$-$CH_2$-$CH_2$-, $CH_3$-CH($CH_3$)-, $CH_3$-($CH_2$)$_3$-, $CH_3$-CH($CH_3$)-$CH_2$-, $CH_3$-$CH_2$-CH($CH_3$)-, $CH_3$-($CH_2$)$_4$-, $CH_3$-($CH_2$)$_6$-, $CH_2$=CH-, $CH_2$=C($CH_3$)-, $CH_3$-CH=CH-,

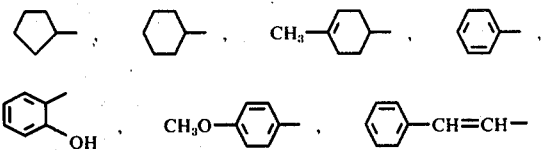

$CH_3$-CH(OH)-, $CH_3$O-$CH_2$-CH(OH)-, COOH-$CH_2$-$CH_2$-, $CH_3$-CO-$CH_2$-$CH_2$- or $CH_3$O-$CH_2$. Existing anhydrides or halides, in particular the chlorides and bromides, of the said acids may also be employed for reaction Ab.

In general, from 1.0 to 10, preferably from 1.5 to 3, moles of the carboxylic acids or their derivatives are employed per mole of III.

The 3,5,5-trimethyl-hepta-2,6-dien-1-yl esters of the formula II obtained from this reaction are new compounds. They exhibit intense herbal, flowery and fruity scents which resemble those of the geranyl esters. They are therefore in themselves outstandingly suitable for se as scents.

If it is intended to employ esters of the formula II as intermediates for the manufacture of lavandulol, the lower aliphatic esters, especially the acetate, or the benzoic acid ester, ie. the benzoate, are employed preferentially.

Preferred esters of the formula II of the manufacture of the lavandulyl esters are those which yield naturally occurring esters of lavandulol, such as the acetate, th caproate, the α-methylbutyrate or the benzoate.

Ac: the hydrolysis of the esters of the formula II to the alcohol IV is carried out by conventional methods, eg. by acid hydrolysis or, more rapidly and more smoothly, by alkaline hydrolysis. Alkaline hydrolysis requuires the use of a molar quantity of alkali, since the alkaline catalyst is neutralized by the carboxylic acid produced. As a result of this neutralization of the carboxylic acid, the latter is removed from the ester equilibrium and hence the rate of saponification is increased. Saponifying agents which may be used are solutions of NaOH, KOH or alkaline earth metal hydroxides in water, but particularly in methanol or ethanol. Further details on acid and alkaline hydrolysis (saponification) are to be found, eg., in Houben-Weyl, vol. 8 (1952), pages 418 - 23 (which is incorporated herein by reference).

Ad: the reaction of III to give 3,5,5-trimethyl-hepta-2,6-dienyl halides may be carried out, eg., in accordance with the process described in Chem. Rev. 56, (1956), pages 801-18 (which are incorporated herein by reference), which give a primary halide. This is generally the case if the reaction mixture is acid. Suitable halogenating agents are, e.g., HBr (aqueous or gaseous), $PBr_3$, $PBr_5$ and $SOBr_2$, or HCl (aqueous or gaseous), $PCl_3$, $PCl_a$, $SOCl_2$, $COCl_2$ and HI. With some halogenating agents, 3,5,5-trimethyl-hepta-1,6-dien-3-yl halides are formed at low temperatures and/or in the presence of basic compounds. These halides may be rearranged to the 3,5,5-trimethyl-hepta-2,6-dien-1-yl halides by treatment with an acid catalyst, analogously to the method described under Aa. The chlorides are preferred.

As an example of the reaction of III to give 3,5,5-trimethyl-hepta-2,6-dien-1-yl chloride, the reaction of III by the process for the manufacture of allyl chlorides in German Patent No. 1,162,354 will be explained in more detail. In this process, III is reacted in the presence of N,N-dialkyl-substituted amides of low molecular weight fatty acids or N-alkyl-substituted lactams, if appropriate in an inert solvent.

The reaction is in general carried out at from about −50° to +50° C, preferably at from −20° to +20° C, and under normal pressure or the slightly superatmospheric pressure under which phosgene is passed in.

Examples of N,N-dialkyl-substituted low molecular weight fatty acid amides are N,N-dimethylformamide, N,N-diethylformamide, N,N-dimethylacetamide and N,N-dibutylpropionamide, whilst N-methylpyrrolidone and N-ethylcaprolactam are examples of N-alkylated lactams. The process is carried out by, eg., placing a mixture of III and the carboxylic acid amide in a suitable solvent and then passing in phosgene, or slowly adding thionyl chloride, at room temperature. However, it is also possible to take a mixture of the carboxylic acid amide and the chlorinating agent and add III. The reaction mixture is worked up by eg., ading water, separating off the organic phase, evaporating the solvent and fractionating the residue, if the latter can be distilled. Suitable solvents are aliphatic and aromatic hydrocarbons, chlorinated hydrocarbons and ethers. The amount of solvent used may be varied within wide limits, up to multi-molar solutions of the allyl alcohol. The process can be carried out without solvent when using a liquid allyl alcohol. The chlorinating agent is suitably used in a slight excess over the allyl alcohol. The N-substituted carboxylic acid amides or N-alkylated lactams are added in amounts of, eg., from 0.02 to 1 mole per mole of chlorinating agent, but it is also possible to use even larger amounts, in which case the acid amide serves as the solvent. Ae: the conversion of the 3,5,5-trimethyl-hepta-2,6-dien-1-yl halides (V) to the corresponding 1-esters is carried out advantageously be reacting V with a salt of the carboxylic acid of which the ester is required in a non-aqueous medium in the presence of catalysts. Catalysts which can be used for this purposes are, eg., quaternary ammonium salts, amines, phosphines, copper compounds, aprotic dipolar compounds or iodides. The reaction is advantageously carried out in the presence of a basic nitrogen compound as the catalyst, and, if appropriate, an ionic iodide and/or polar aprotic compounds as co-catalysts.

Suitable salts of the carboxylic acids of the formula R-COOH, in which R has the above meanings, are the alkali metal salts, alkaline earth metal salts and ammonium salts, especially the sodium salts.

A basic nitrogen compound for use according to the invention is ammonia, hydrazine, hydroxylamine, formamidine or guanidine or one of their alkyl-substituted derivatives which, because of their electronic structure and their steric configurations, can be quaternized with terpene-allyl chlorides under the reaction conditions. Suitable derivatives of ammonia are primary, secondary or tertiary amines which may be aliphatic, aromatic or heterocyclic. Examples of basic nitrogen compounds which may be employed are triethylamine, tributylamine, phenylhydrazine, hydroxylamine, guanidine, acetamidine and diazabicyclononene.

Preferred quaternary salts of the basic nitrogen compounds are those obtained from V and the basic nitrogen compound, especially those obtained from V and ammonia or primary, secondary or tertiary amines. In addition, however, compounds containing any other radicals can also be used, provided at least one of the radicals as a fairly long chain, i.e., of 4 or more carbon atoms, tetrabutylammonium iodide being a specific example.

Polar aprotic comounds which may be used are in particular those which have a dipole moment greater than 2.5 debye and a dielectric constant greater than 15 and which melt below 60° C, eg. N,N-dialkylamides, sulfoxides, sulfones, nitriles, nitro compounds, ketones, carbonates, phosphoric acid esters and amides, provided they are stable under the reaction conditions. Examples which may be mentioned are dimethylformamide, dimethylsulfoxide, sulfolan, acetonitrile, hexamethylphosphoric acid triamide, propylene carbonate, trimethyl phosphate, nitromethane and acetone. Ionic iodides which may be used are, in particular, alkali metal iodides, ammonium iodides or tetraalkylammonium iodides. Particularly good results are obtained when both polar aprotic compounds and ionic iodides are used as co-catalysts.

The reaction according to the invention may be carried out in inert solvents such as hydrocarbons, chlorinated hydrocarbons or ethers, but it is not absolutely essential to use solvents.

In general, the process is carried out by keeping the reaction mixture, consisting of V, the salt of an aliphatic carboxylic acid, the basic nitrogen compound and, optionally, the polar aprotic compound and/or the ionic iodide and, optionally, the inert solvent, at the reaction temperature for the appropriate reaction time, whilst stirring.

The reaction time is from about 10 minutes to 10 hours, preferably from 0.5 to 6 hours, depending on the reaction temperature, catalyst and co-catalyst.

The reaction temperature may be from 0° C to 100° C, preferably from 40° to 80° C.

The molar ratio of V to salt of the carboxylic acid is in general from 1 : 5 to 1 : 1, preferably from 1 : 2 to 1 : 1.

The basic nitrogen compound is in general used in an amount of from 0.5 to 20 mole%, preferably from 1 to 10 mole%, based on V.

The polar aprotic compound is in general employed in an amount of from 1 to 100% by weight, preferably from 5 to 20% by weight, based on V employed.

The ionic iodide is in general employed in an amount of from 0.5 to 20 mole%, preferably from 1 to 10 mole%, based on V.

Bf and Bg: the rearrangement of 3,5,5-trimethyl-hepta-2,6-dien-1-ol (IV) to lavandulol or of the esters of the formula II to the corresponding lavandulyl esters is an essential part of the process according to the invention. Brack and Schinz (Helv. Chim. Acta 34, (1951), pages 2009 et seq., especially 2010), who in their work on alternative methods of manufacture of lavandulol arrived at the alcohol VI, also attempted to rearrange VI to lavandulol. However, they described their attempt as follows: "To effect rearrangement, the alcohol VI was heated at 300° C in a bomb tube. However, this in the main produced unsaturated hydrocarbons, as a result of elimination of water, whilst under milder conditions the substance remained unchanged." In the experiments at 300° C, the yield of lavandulol was only 1.25% of theory.

It was therefore extremely surprising that it should prove possible to rearrange the alcohol VI to lavandulol, in high yield and high purity, by heating at from 150° to 250° C, preferably from 170° to 200° C. An even more surprising fact was that it also proved possible to rearrange the esters of VI with carboxylic acids to the corresponding lavandulyl esters in the same way.

The heating of the compounds of the formula II in accordance with the invention can be effected without solvents but is preferably effected in an inert solvent. Inert solvents which may be used are all solvents which do not react with the compounds of the formula II at the reaction temperature, eg. aliphatic and aromatic hydrocarbons, chlorinated hydrocarbons, ethers, esters, nitriles, ketones, alcohols and amides. If low-boiling solvents are used, it is necessary to work under the autogenous pressure of the solvent, in a closed system, in order to reach the reaction temperature. Solvents which boil above the reaction temperature are preferred, eg. diphenyl ether, nitrobenzene, tetralin, sulfolan, squalane, tricresyl phosphate, dibutyl tetrachlorophthalate, bis-2-ethylhexyl sebacate, dibutyl phthalate and dibenzyl ether, but especially solvents of such high boiling point (in excess of 250° C at atmospheric pressure that lavandulol or its esters can be distilled off easily without contamination by solvents; examples of such latter solvents are paraffin oils, silicone oils, white oils, groundnut oils, polyethylene glycol, ethers of polyethylene glycols, and phthalic acid esters.

The volume of solvent may be from 0.5 to 50, preferably from 3 to 10, times the volume of the compound of the formula II. The reaction is advantageously carried out under an inert gas, eg., nirogen. The presence of acid impurities during the heating process should be avoided. The process may be carried out continuously.

The rearrangement gives lavandulol and lavandulyl esters in very good yields and in excellent purity.

The yields of lavandulol are less good if the new 3,5,5-trimethyl-hepta-1,6-dien-3-ol is heated, in bulk or as a solution in an inert solvent, at from 150° to 250° C, preferably from 180° to 220° C.

Solvents which may be used for this purpose are all solvents mentioned for the above step B, and here again solvents which boil above the reaction temperature are preferred.

Using the process according to the invention, it is possible to manufacture the desirable product lavandulol, and the lavandulyl esters which are also of great interest as scents, and even previously unknown lavandulyl esters, from easily obtainable starting compounds, by a simple method and in good yields and excellent purity. Both the new starting compound 3,5,5-trimethylhepta-1,6-dien-3-ol and the new 3,5,5-trimethyl-hepta-2,6-dien-1-yl esters formed as intermediates may be employed in the perfumery industry because of their scent properties.

The Examples which follow further explain the present invention and show how it may be carried out in practice.

EXAMPLE 1

Manufacture of the new starting compound:

252 g (2.0 moles) of 4,4-dimethyl-5-hexen-2-one are added dropwise in 2 hours to 2,000 ml of a 1.4 molar solution of vinyl-magnesium chloride (2.8 moles) in tetrahydrofuran (THF) at from 16° to 20° C, and the reaction mixture is stirred for 2 hours at 20° C. After hydrolysis with 280 ml of water, inorganic salts are filtered off, the filtrate is concentrated and the crude product is fractionated. 290 g (94%) of 3,5,5-trimethylhepta-1,6-dien-3-ol pass over at from 65° to 68° C/1 mm Hg. Scent: intense and menthol-like.

EXAMPLE 2

15.4 g (0.1 mole) of 3,5,5-trimethyl-hepta-1,6-dien-3-ol, 75 ml of water and 0.15 g of p-toluenesulfonic acid are stirred vigorously for 2 hours at 100° C. The organic phase is separated off, washed neutral, concentrated and distilled. From 35° to 68° at 0.3 mm Hg, 14.9 g of a colorless product pass over containing, according to gas chromatography, 22% of unconverted starting alcohol (corresponding to 79% conversion) and 58% of 3,5,5-trimethyl-hepta-2,6-dien-1-ol, ie 71.5% of theory, based on complete conversion (Aa).

EXAMPLE 3

154 g (1.0 mole) of 3,5,5-trimethyl-hepta-1,6-dien-3-ol and 1.0 g of ammonium molybdate are heated at 160° C for 90 minutes. The resulting product contains, according to gas chromatography, 8% of triene, 81% of 3,5,5-trimethyl-hepta-2,6-dien-1-ol and 9.5% of starting material (Aa).

EXAMPLE 4

77 g (0.5 mole) of 3,5,5-trimethyl-hepta-1,6-dien-3-ol are added dropwise to 102 g (1.0 mole) of acetic anhydride and 5 ml of BF$_3$-glacial acetic acid in 10 minutes at 0° C and the batch is stirred for 100 minutes at 0° C. It is then repeatedly washed with warm water and the aqueous phase is extracted with three times 100 ml of ether. The organic phase is washed neutral, dried and concentrated. 74 g of 3,5,5-trimethyl-hepta-2,6-dien-1-yl acetate pass over at from 132° to 135° C/23 mm Hg. This corresponds to a yield of 75.5% of theory, based on 3,5,5-trimethyl-hepta-1,6-dien-3-ol (Ab).

EXAMPLE 5

154 g (1.0 mole) of 3,5,5-trimethyl-hepta-1,6-dien-3-ol and 210 g (2.1 moles) of acetic ahydride are refluxed for 6 hours. On working up analogously to Example 7, 124 g 3,5,5-trimethyl-hepta-2,6-dien-1-yl acetate are obtained. This corresponds to a yield of 64.3% of theory (Ab).

EXAMPLE 6

A solution of 392 g (2.0 moles) of 3,5,5-trimethyl-hepta-2,6-dienyl acetate, 200 ml of methanol and 320 g (4.0 moles) of 50% strength NaOH is stirred for one hour at 50° C. After adding 1,500 ml of water, the organic phase is separated off, washed and distilled. 295 g (96%) pure 3,5,5-trimethyl-hepta-2,6-dien-1-ol pass over at from 67° to 68° C/0.5 mm Hg. Scent: herbs and fresh hay (Ac).

EXAMPLE 7

In the course of three hours, 300 g (3.0 moles) of phosgene are passed into a solution of 385 g (2.5 moles) of 3,5,5-trimethyl-hepta-1,6-dien-3-ol and 220 g (3.0 moles) of dimethylformamide in 1,200 ml of benzene at from −10° to 0° C and the reaction mixture is then stirred for 60 minutes at −10° C. The benzene phase is washed with water, 10% strength NaOH and again with water. After distilling off the benzene, 414 g (96.5%) crude 3,5,5-trimethyl-hepta-2,6-dienyl chloride are obtained as a pale yellow oil (Ad).

EXAMPLE 8

414 crude 3,5,5-trimethyl-hepta-2,6-dienyl chloride (91% pure according to gas chromatography, and therefore corresponding to 2.2 moles) are stirred for four hours at 60° C with 290 g (3.75 moles) of anhydrous sodium acetate, 12 ml of triethylamine, 12 g of sodium iodide and 33 ml of dimethylformamide (DMF). After adding 1,100 ml of water, the organic phase is separated off, washed and distilled. 396 g (81%, based on 3,5,5-trimethyl-hepta-1,6-dien-3-ol) of 3,5,5-trimethylhepta-2,6-dienyl acetate ($n_D^{20}$ = 1.4549) pass over at from 61 to 63° C/0.3 mm Hg, as a pale yellow liquid. Scent resembling geranyl acetate, but substantially more fruity (Ae).

EXAMPLE 9

345 g (1.81 moles) of crude 3,5,5-trimethyl-hepta-2,6-dien-1-yl chloride (90.4% pure according to gas chromatography), 3 moles of the sodium salts of the carboxylic acids shown in the table which follows, 10 g of NaI, 10 ml of triethylamine and 200 ml of DMF are stirred for 4 hours at 80° C. The resulting reaction mixture is poured into 1 l of water, the organic phase is separated off and the aqueous phase is extracted by shaking with three times 150 ml of ether. The combined organic phases are washed neutral, dried, freed from the solvent and fractionated through a short column. This reaction gives the new 3,5,5-trimethyl-hepta-2,6-dien-1-yl esters of the carboxylic acids of which the sodium salts were employed (Ae).

The results are shown in the table which follows:

| Na salt of or 3,5,5-trimethyl-hepta-2,6-dien-1-yl ester of | Yield of ester (g) | (% of theory) | Boiling point/mm Hg (° C) | $N_D^{20}$ | Odor |
|---|---|---|---|---|---|
| Formic acid | 283 | 86 | 68–72/0.5 | 1.4559 | Herbal, fresh, green |
| Propionic acid | 348 | 91.5 | 88–91/0.15 | 1.4547 | Fruity (pineapple), flowery, green |
| Butyric acid | 357 | 88 | 100–102/0.3 | 1.4535 | Herbal, flowery, buttery |
| Isobutyric acid | 363 | 89.5 | 80–83/0.1 | 1.4510 | Herbal, fruity |
| Isovaleric acid | 354 | 82 | 84–86/0.1 | 1.4521 | Valerian-like |
| -Methylbutyric acid | 392 | 91 | 92–98/0.2 | 1.4523 | Acidic, fruity, plum-like |
| Caproic acid | 402 | 88.5 | 111–115/0.1 | 1.4561 | Slightly flowery, oily |
| Benzoic acid | 434 | 93 | 136–141/0.1 | 1.5125 | Slightly flowery |
| Dimethacrylic acid | 314 | 74 | 82–83/0.1 | | |
| Cinnamic acid | 432 | 84 | 135–137/0.1 | | |

EXAMPLE 10 a. 50 g of 3,5,5-trimethyl-hepta-2,6-dien-1-ol in 200 ml of paraffin oil are heated at 200° C under nitrogen for 8 hours, On subsequent distillation, 44 g of a colorless product, containing 94.5% of lavandulol according to gas chromatography, pass over at from 85° to 100° C/15 mm Hg (Bf).

b. 100 g of 3,5,5-trimethyl-hepta-2,6-dienol and 0.5 g of dimethylaniline are heated in bulk at 190° C under nitrogen for 20 hours. Fractionation of the product gives 54 g, corresponding to 54% of theory, of boiling at from 71° to 73°/1 mm Hg (Bf).

EXAMPLE 11

A solution of 20 g of 3,5,5-trimethyl-hepta-2,6-dien-1-ol in 100 ml of one of the solvents shown in the table below is heated at 200° C for 7 hours. The lavandulol obtained is then distilled from the reaction mixture, through a short column, at a boiling point of 90° to 100°C/15 mm Hg. The table below contains data on the yields of lavandulol obtained in the various solvents (Bf).

| Solvent | Yield of lavandulol (g) | (% of theory) |
|---|---|---|
| Diphenyl ether | 15.7 | 78.5 |
| Polyethylene glycol | 16.2 | 81.0 |
| Silicone oil | 15.4 | 77.0 |

EXAMPLE 12 a. 50 g of 3,5,5-trimethyl-hepta-2,6-dienyl acetate in 250 ml of one of the solvents in the table below are heated at 190° C under nitrogen for 25 hours. Lavandulyl acetate is then distilled off through a short column at from 72° to 75° C/0.5 mm Hg. According to a gas chromatogram, and nuclear resonance spectroscopy, the product contains virtually none of the starting material. The yields achieved in each particular solvent are shown below.

| Solvent | Yield of lavandulyl acetate (g) | (% of theory) |
|---|---|---|
| Paraffin oil | 41 | 82 |
| Silicone oil | 38 | 76 |
| Groundnut oil | 46 | 92 |

It is found from gas chromatography and nuclear resonance spectroscopy that the product contains ≤ 2% of 3,5,5-trimethylhepta-2,6-dienyl acetate and ≤ 1% of isolavandulyl acetate (Bg).

b. If the method described under (a) is followed but only 50 ml of paraffin oil are used instead of 250 ml, only 33 g of lavandulyl acetate are obtained, corresponding to a yield of 66% of theory.

c. If the method described under (a) is followed, but without using a solvent, only 24 g of lavandulyl acetate are obtained, corresponding to a yield of 48% of theory.

d. 100 g of 3,5,5-trimethyl-hepta-2,6-dienyl acetate in 400 ml of paraffin oil are heated to 190° C for 24 hours. Subsequent distillation as in Example 6 gives 86 g of lavandulyl acetate, corresponding to 86% of theory.

The distillation residue, consisting essentially of paraffin oil, is again heated with 100 g of 3,5,5-trimethyl-hepta-2,6-dienyl acetate at 190° C for 24 hours. Distillation again gives 86 g (corresponding to 86% of theory) of lavandulyl acetate. A further repetition of the procedure gives 84 g of lavandulyl acetate, corresponding to 84% of theory.

EXAMPLE 13

A solution of 100 g of the 3,5,5-trimethyl-hepta-2,6-dien-1-yl esters of the carboxylic acids indicated in the table which follows in 500 ml of paraffin oil is heated at 190° C for 20 hours. The reaction product is then distilled from the paraffin oil through a short column. The yields and physical data of the corresponding lavandulyl esters obtained in this reaction are shown in the table which follows (Bg).

| 3,5,5-Trimethyl-hepta-2,6-dien-1-yl ester or lavandulyl ester of | Yield of lavandulyl esters (g) = (% of theory) | Boiling point/ mm Hg (° C) | $n_D^{25}$ |
|---|---|---|---|
| Formic acid | 78 | 58–60/0.1 | |
| Propionic acid | 83 | 63–65/0.1 | 1.4516 |
| Butyric acid | 86 | 67–70/0.1 | 1.4526 |

-continued

| 3,5,5-Trimethyl-hepta-2,6-dien-1-yl ester or lavandulyl ester of | Yield of lavandulyl esters (g) = (% of theory) | Boiling point/ mm Hg (° C) | $n_D^{25}$ |
|---|---|---|---|
| Caproic acid | 81 | 85–88/0.1 | 1.4560 |
| Benzoic acid | 87 | 86–88/0.1 | 1.5385 |

EXAMPLE 14

15.4 g (0.1 mole) of 3,5,5-trimethyl-hepta-1,6-dien-3-ol and 50 ml of paraffin oil are heated at 200° C for 70 minutes. According to gas chromatography, the product obtained contains 74% of trienes, 15% of starting material and 11% of lavandulol (C).

We claim:
1. A process for the manufacture of compounds of the formula I

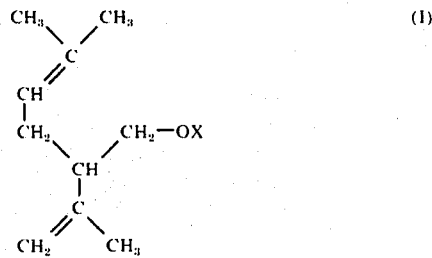

in which X is H or -CO-R, wherein R is H, HOOC-CH$_2$-CH$_2$-, a saturated or olefinically unsaturated aliphatic hydrocarbon radical of up to 8 carbon atoms, a saturated or olefinically unsaturated cycloaliphatic hydrocarbon radical of up to 8 carbon atoms or an aromatic hydrocarbon radical of 6 to 8 carbon atoms, each of which radicals may bear as substituents -OH, methoxy or acetyl groups in which process
   A. the compound 3,5,5-trimethyl-hepta-1,6-dien-3-ol is converted to a 3,5,5-trimethyl-hepta-2,6-diene derivative of the formula II

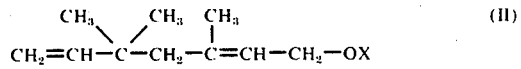

in which X has the above meanings, and
   B. the resulting compound of the formula II is heated, optionally in a solvent which is inert under the reaction conditions, at 150° to 250° C.

2. A process as claimed in claim 1 for the manufacture of lavandulol as the compound of the formula I in which X is H, wherein, in reaction step A, 3,5,5-trimethyl-hepta-1,6-dien-3-ol is converted to 3,5,5-trimethyl-hepta-2,6-dien-1-ol by treatment with an acid catalyst at from −50° to +200° C in the liquid phase.

3. A process as claimed in claim 1, for the manufacture of lavandulol as the compound of the formula I, in which X is H, wherein, in reaction step A, 3,5,5-trimethyl-hepta-1,6-dien-3-ol is converted to 3,5,5-trimethyl-hepta-2,6-dien-1-ol by first reacting said 3,3,5-trimethyl-hepta-1,6-dien-3-ol in the presence of an acid catalyst with a carboxylic acid of the formula R-COOH, in which R has the meanings given in claim 1, or with the corresponding carboxylic acid anhydride or carboxylic acid halide and then hydrolyzing, the resulting 3,5,5-trimethyl-hepta-2,6-diene derivative of the formula II, in which X is -CO-R.

4. A process as claimed in claim 1 for the manufacture of lavandulol as the compound of the formula I, in which X is H, wherein, in reaction step A, 3,5,5-trimethyl-hepta-1,6-dien-3-ol is converted to 3,5,5-trimethyl-hepta-2,6-dien-1-ol by first converting said 3,3,5-trimethyl-hepta-1,6-dien-3-ol by conventional methods to a 3,5,5-trimethyl-hepta-2,6-dien-1-yl halide, which is then reacted, with an alkali metal salt, alkaline earth metal salt or ammonium salt of the carboxylic acid R-COOH, in which R has the above meanings, in a non-aqueous medium in the presence of a catalyst, to give the 3,5,5-trimethyl-hepta-2,6-diene derivative of the formula II, in which X is -CO-R, and this derivative is hydrolyzed.

5. A process as claimed in claim 1 for the manufacture of lavandulyl esters, having the formula I, in which X is -CO-R, R having the meanings given in claim 1, wherein, in reaction step A, 3,5,5-trimethyl-hepta-1,6-dien-3-ol is converted, by reaction with a carboxylic acid of the formula R-COOH, in which R has the meanings given in claim 1, or with the corresponding carboxylic acid anhydride or carboxylic acid halide, in the presence of an acid catalyst, to a 3,5,5-trimethyl-hepta-2,6-diene derivative of the formula II, in which X is -CO-R.

6. A process as claimed in claim 1 for the manufacture of lavandulyl esters having the formula I, in which X is -CO-R, R having the meanings given in claim 1, wherein, in reaction step A, 3,5,5-trimethyl-hepta-1,6-dien-3-ol is converted to a 3,5.5-trimethyl-hepta-2,6-dien-3-ol derivative of the formula II, in which X is -CO-R, by first converting said 3,3,5-trimethyl-hepta-1,6-diene-3-ol to 3,5,5-trimethyl-hepta-1,6-dien-1-yl chloride or bromide and reacting said chloride or bromide with an alkali metal salt, alkaline earth metal salt or ammonium salt of a carboxylic acid R-CO-OH in a non-aqueous medium in the presence of a catalyst.

7. A process as claimed in claim 1 for the manufacture of lavandulyl esters having the formula I, in which X is -CO-R, R having the meanings given in claim 1, wherein, in reaction step A, 3,5,5-trimethyl-hepta-1,6-dien-3-ol is converted, by treatment with an acid catalyst at from −50° to +200° C, in the liquid phase, to 3,5,5-trimethyl-hepta-2,6-dien-1-ol, and esterifying the latter compound with a carboxylic acid of the formula R-CO-OH, R having the meanings given in claim 1.

8. A process for the manufacture of lavandulol, wherein 3,5,5-trimethyl-hepta-1,6-dien-3-ol, optionally in solution in an inert solvent, is heated at 150° to 250° C.

9. A process as claimed in claim 1, wherein, in process step B, the compound of the formula II is heated, at atmospheric pressure, in an inert solvent which boils above the reaction temperature.

10. A process as claimed in claim 1 for the manufacture of lavandulol as the compound of formula I in which X is H wherein, in reaction step A, 3,5,5-trimethyl-hepta-1,6-dien-3-ol is converted to 3,5,5-trimethyl-hepta-2,6-dien-1-ol by heating said 3,3,5-trimethyl-hepta-1,6-dien-3-ol in the presence of a catalyst of a transition metal of sub-groups 5 to 7 of the Periodic Table of the Elements at 50° to 250° C.

11. A process as claimed in claim 1 for the manufacture of lavandulyl esters having the formula I, in which X is -CO-R, R having the meanings given in claim 1, wherein, in reaction step A, 3,5,5-trimethyl-hepta-1,6- dien-3-ol is converted by heating said 3,3,5-trimethyl-hepta-1,6-dien-3-ol in the presence of a catalyst of a transition metal of sub-groups 5 to 7 of the Periodic Table of the Elements, at 50° to 250° C, and esterifying the latter compound with a carboxylic acid of the formula R-CO-OH, R having the meanings given in claim 1.

12. A process as claimed in claim 8 wherein said 3,3,5-trimethyl-hepta-1,6-dien-3-ol is heated at 180° to 220° C.

* * * * *

UNITED STATES PATENT AND TRADEMARK OFFICE
CERTIFICATE OF CORRECTION

PATENT NO. : 3,997,577
DATED : December 14, 1976
INVENTOR(S) : von FRAUNBERG

It is certified that error appears in the above-identified patent and that said Letters Patent are hereby corrected as shown below:

In Column 14, Line 8, delete " by conventional methods "

Signed and Sealed this

Eleventh Day of July 1978

[SEAL]

Attest:

RUTH C. MASON
Attesting Officer

DONALD W. BANNER
Commissioner of Patents and Trademarks